(12) United States Patent
Menn et al.

(10) Patent No.: US 10,342,521 B2
(45) Date of Patent: Jul. 9, 2019

(54) SPECIMEN REMOVAL DEVICE WITH GAS VENTING

(71) Applicant: Covidien LP, Mansfield, MA (US)

(72) Inventors: Dmitri Menn, Yulee, FL (US); Gene A. Stellon, Burlington, CT (US)

(73) Assignee: Covidien LP, Mansfield, MA (US)

( * ) Notice: Subject to any disclaimer, the term of this patent is extended or adjusted under 35 U.S.C. 154(b) by 317 days.

(21) Appl. No.: 15/155,145

(22) Filed: May 16, 2016

(65) Prior Publication Data

US 2016/0256144 A1    Sep. 8, 2016

Related U.S. Application Data

(63) Continuation-in-part of application No. 13/396,999, filed on Feb. 15, 2012, now Pat. No. 9,364,202.

(60) Provisional application No. 61/451,755, filed on Mar. 11, 2011.

(51) Int. Cl.
*A61B 17/00* (2006.01)
*A61B 90/00* (2016.01)

(52) U.S. Cl.
CPC ............... *A61B 17/00234* (2013.01); *A61B 2017/00287* (2013.01); *A61B 2090/0816* (2016.02)

(58) Field of Classification Search
CPC .... A61B 2017/00287; A61B 17/00234; A61B 2090/0816
See application file for complete search history.

(56) References Cited

U.S. PATENT DOCUMENTS

| 4,428,375 | A | 1/1984  | Ellman         |
|-----------|---|---------|----------------|
| 5,037,379 | A | 8/1991  | Clayman et al. |
| 5,074,867 | A | 12/1991 | Wilk           |
| 5,176,687 | A | 1/1993  | Hasson et al.  |
| 5,190,542 | A | 3/1993  | Nakao et al.   |
| 5,215,521 | A | 6/1993  | Cochran et al. |
| 5,224,930 | A | 7/1993  | Spaeth et al.  |
| 5,354,303 | A | 10/1994 | Spaeth et al.  |
| 5,368,597 | A | 11/1994 | Pagedas        |
| 5,465,731 | A | 11/1995 | Bell et al.    |
| 5,647,372 | A | 7/1997  | Tovey et al.   |
| 5,735,289 | A | 4/1998  | Pfeffer et al. |
| 5,759,187 | A | 6/1998  | Nakao et al.   |

(Continued)

FOREIGN PATENT DOCUMENTS

| DE | 4204210 A1  | 8/1992 |
|----|-------------|--------|
| DE | 19624826 A1 | 1/1998 |

(Continued)

OTHER PUBLICATIONS

Merriam-Webster.com, Definition of porosity, downloaded Dec. 7, 2015, Merriam-Webster.com, 4 pages.

(Continued)

*Primary Examiner* — David J. McCrosky (57) ABSTRACT

A removal pouch that is utilized for removing body tissue from the interior of the body as part of a minimally invasive surgical procedure. The specimen removal pouch includes an elongated body and a gas vent. The elongated body has an interior portion to collect specimen from a body cavity of a patient. The gas vent is configured to allow passage of gas from the interior portion of the elongated body to an external environment during removal of the pouch from within the body cavity of a patient.

9 Claims, 7 Drawing Sheets

(56) References Cited

U.S. PATENT DOCUMENTS

| | | | |
|---|---|---|---|
| 5,908,429 A | 6/1999 | Yoon | |
| 6,007,546 A | 12/1999 | Snow et al. | |
| 6,406,440 B1 | 6/2002 | Stefanchik | |
| 7,115,125 B2 | 10/2006 | Nakao et al. | |
| 7,588,545 B2 | 9/2009 | Cohen et al. | |
| 7,762,959 B2 | 7/2010 | Bilsbury | |
| 9,033,995 B2 * | 5/2015 | Taylor | A61B 17/00234 606/114 |
| 9,364,202 B2 | 6/2016 | Menn et al. | |
| 2002/0082516 A1 | 6/2002 | Stefanchik | |
| 2005/0043750 A1 | 2/2005 | Scott et al. | |
| 2008/0177214 A1 | 7/2008 | Robertsson et al. | |
| 2009/0182292 A1 | 7/2009 | Egle et al. | |
| 2011/0190781 A1 * | 8/2011 | Collier | A61B 17/00234 606/114 |

FOREIGN PATENT DOCUMENTS

| | | | |
|---|---|---|---|
| EP | 2353510 A2 | 8/2011 | |
| GB | 2460099 A | 11/2009 | |
| WO | 0135831 A1 | 5/2001 | |
| WO | 2009055791 A2 | 4/2009 | |

OTHER PUBLICATIONS

Merriam-Webster.com, Definition of porous, downloaded Dec. 7, 2015, Merriam-Webster.com, 5 pages.

European Search Report for EP 12158873.5-1269 dated Jul. 12, 2012 (9 pages).

European Search Report corresponding to European Application No. 13190025.0, dated Feb. 24, 2014; 5 pages.

\* cited by examiner

SPECIMEN REMOVAL DEVICE WITH GAS VENTING

CROSS-REFERENCE TO RELATED APPLICATIONS

This application is a continuation-in-part of U.S. patent application Ser. No. 13/396,999, now U.S. Pat. No. 9,634,202, filed Feb. 15, 2012, which claims benefit of and priority to U.S. Provisional Application No. 61/451,755 filed Mar. 11, 2011, and the disclosures of each of the above-identified applications are hereby incorporated by reference in their entirety.

BACKGROUND

Technical Field

The present disclosure relates generally to a specimen removal device for use during a surgical procedure, and more particularly, the present disclosure relates to a specimen removal device including a pouch having a gas vent.

Description of Related Art

Laparoscopic and endoscopic surgical procedures are minimally invasive procedures in which operations are carried out within the body by using elongated instruments inserted through small entrance openings or incisions in body tissue. The initial opening in the body tissue to allow passage of the endoscopic or laparoscopic instruments to the interior portion of the body cavity may be a natural passageway of the body, or it can be created by a tissue-piercing instrument, for example, but not limited to a trocar. Because the endoscopic or laparoscopic cannulae, instrumentation, and any required punctures or incisions are relatively narrow, endoscopic or laparoscopic surgery is less invasive as compared to conventional surgical procedures in which the surgeon is required to cut open large areas of body tissue. Therefore, laparoscopic or endoscopic surgery minimizes trauma to the patient and reduces patient recovery time.

Minimal invasive procedures may be used for partial or total removal of a body specimen, e.g., body tissue or organs, from an interior portion of a body cavity, e.g. nephrectomy, cholecystectomy, and other such procedures. During such procedures, it is common that a cyst, tumor, tissue, foreign object or organ must be removed via the access opening in the skin, or through a cannula. Various types of collection devices, for example, pouches or sacs, have been disclosed to facilitate this procedure.

In certain situations, it is often difficult to remove a pouch or sac through a small laparoscopic incision and/or cannula when, in addition to the collected specimen, air is trapped therewithin. The trapped air increases the volume of the pouch, thus, making the pouch large and difficult to remove through a small opening, for example, a small incision and a cannula. During removal, the enlarged pouch sometimes tears or ruptures, which causes the collected specimen to spill inside the abdominal cavity. The spilled specimen may sometimes cause infection(s) or spreading of cancerous cells inside the abdominal cavity.

SUMMARY

Disclosed herein is a removal pouch that is utilized for removing body tissue from the interior of the body as part of a minimally invasive surgical procedure. The specimen removal pouch includes an elongated body and a gas vent. The elongated body has an interior portion to collect specimen from a body cavity of a patient. A portion of the elongated body includes a gas vent that is configured to remove gas from the interior portion of the elongated body during removal of the pouch from within the body cavity of a patient.

In embodiments, the gas vent may include a hydrophobic material and/or may be porous. The interior portion and an exterior portion of the specimen removal pouch also may be coated with a lubricous material, for example, a hydrogel.

In other embodiments, the gas vent may be positioned about the distal closed end of the elongated body and/or may include one or more filter elements.

In other embodiments, the specimen removal pouch is utilized with a specimen removal device for removing and confining tissue from a surrounding tissue in a body cavity during a surgical procedure. The specimen removal device includes an elongated tubular member, a pouch, and a drawstring. The elongated tubular member has an open distal end and a bore therein that is operably coupled to a housing. The housing has a handle assembly that is operably coupled to a support member via a drive rod. The pouch is operably coupled to the support member and having an interior portion for receiving tissue from the body cavity. As described above, the pouch includes a gas vent and an elongated portion that has a proximal open end and a distal open end. The gas vent has a proximal open end and a distal closed end. The proximal open end is coupled to the distal open end of the elongated portion and a portion of the gas vent includes a hydrophobic material for removing gas from the interior portion of the pouch. The drawstring is operatively coupled to the proximal open end of the elongated portion wherein pulling the drawstring in a proximal direction causes the pouch to move in a proximal direction and the proximal open end of the elongated portion to substantially close.

In embodiments, the support member may include a pair of resilient support portions such that each of the resilient support portions has a first end attached to the drive rod.

In other embodiments, the device may include a locking tab that has a locking position that is in engagement with the drive rod and a releasing position that is disengaged from the drive rod. The handle assembly may also slidably support the locking tab.

These and other features of the current disclosure will be explained in greater detail in the following detailed description of the various embodiments.

BRIEF DESCRIPTION OF THE DRAWINGS

The above and other aspects, features, and advantages of the present disclosure will become more apparent in light of the following detailed description when taken in conjunction with the accompanying drawings in which.

Other features of the present disclosure will become apparent from the following detailed description, taken in conjunction with the accompanying drawings, which illustrate, by way of example, the principles of the present disclosure.

DETAILED DESCRIPTION

Embodiments of the present disclosure will now be described in detail with reference to the drawings, in which like reference numerals designate identical or corresponding elements in each of the several views. As used herein, the term "distal" refers to the portion of the instrument which is further from the user while, the term "proximal" refers to that portion of the instrument which is closer to the user. As used herein, the phrase "external environment" refers to the area outside the instrument or any of the embodiments of the present disclosure. In the following description, well-known functions or constructions are not described in detail to avoid obscuring the present disclosure in unnecessary detail.

As used herein with reference to the present disclosure, the terms "laparoscopic" and "endoscopic" are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures.

Generally, the present disclosure is directed to a pouch made of an elastomeric membrane (e.g., thermoplastic polyurethane) that may be used in conjunction with an endoscopic specimen removal device. In embodiments, at least a portion of the pouch is made from a hydrophobic filter material or element (e.g., polyolefin fibers), which allows the pouch to release or vent air that is trapped within an interior portion of the pouch to an external environment, while retaining fluid or other matter (e.g., contaminated tissue) within the pouch. Further, the trapped air is effectively vented from within the pouch to allow the pouch to decrease in size and facilitate removal through a small laparoscopic incision and/or cannula. The present disclosure also provides a pouch including a lubricious coating on an inside and outside portion the pouch material.

Figure 1A:
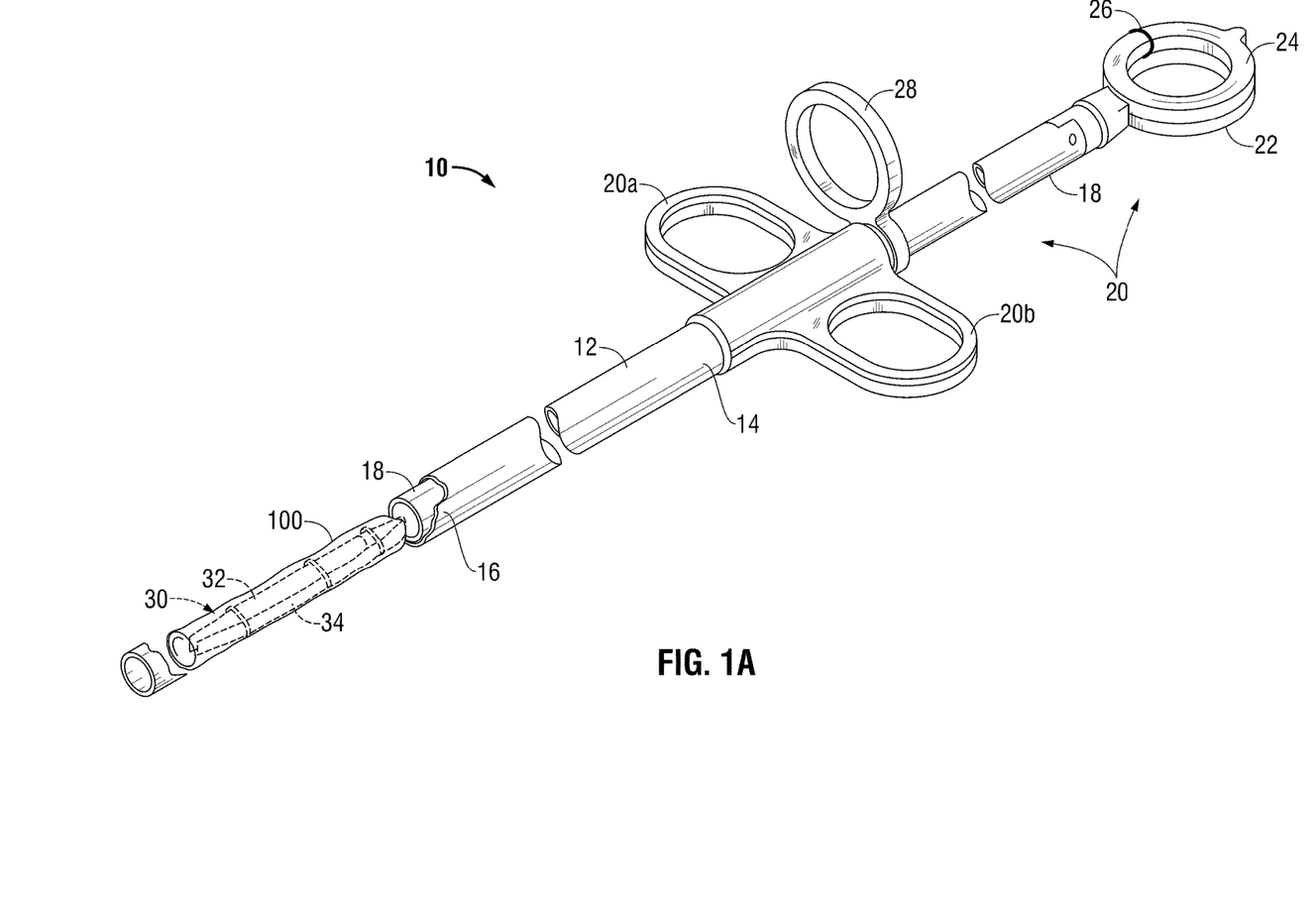
FIG. 1A is a perspective view of a specimen removal device including a pouch according to the present disclosure shown in an undeployed configuration.
Figure 1B:
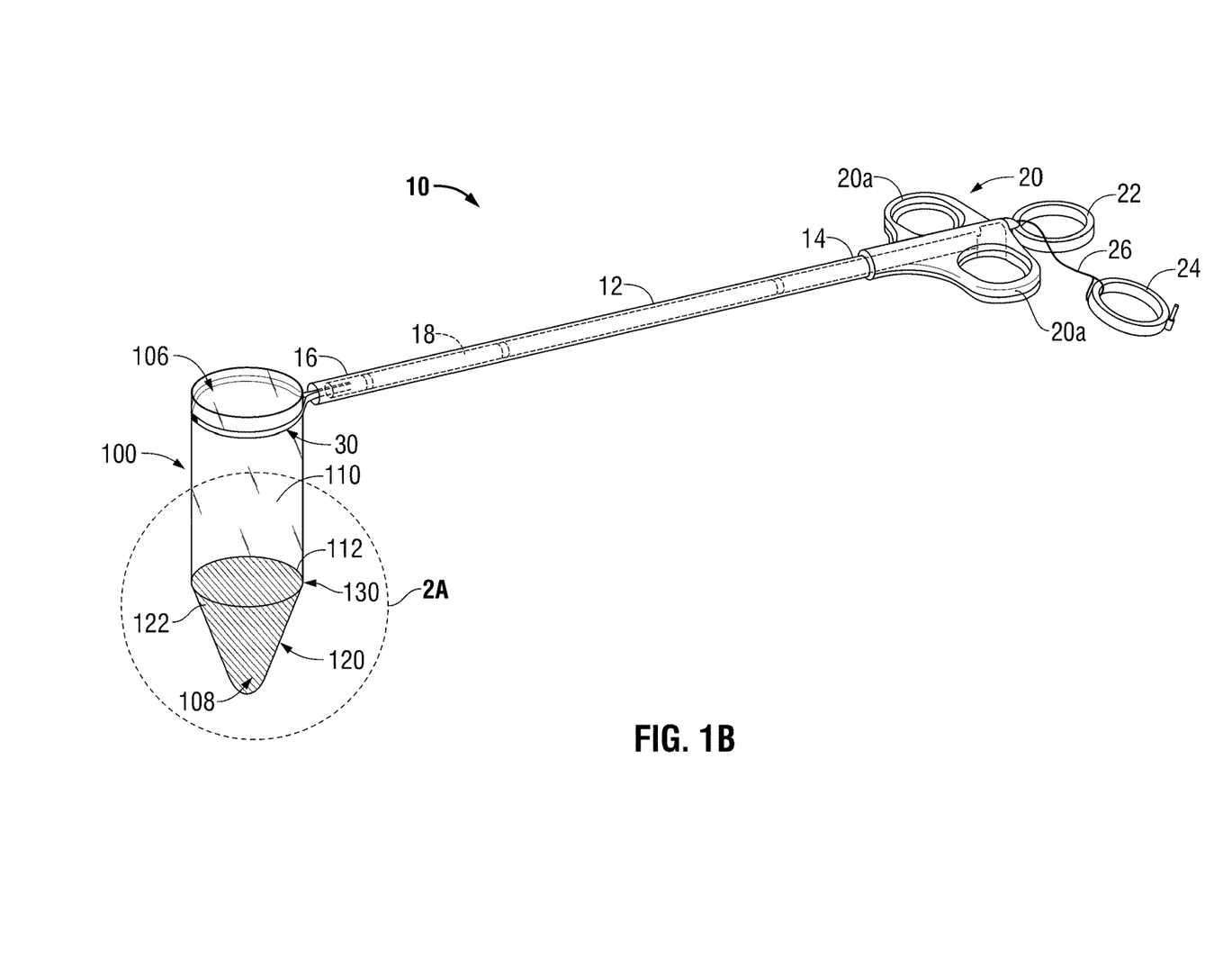
FIG. 1B is a perspective view of the specimen removal device of FIG. 1A including an embodiment of a pouch according to the present disclosure shown in a deployed configuration.
Figure 1C:
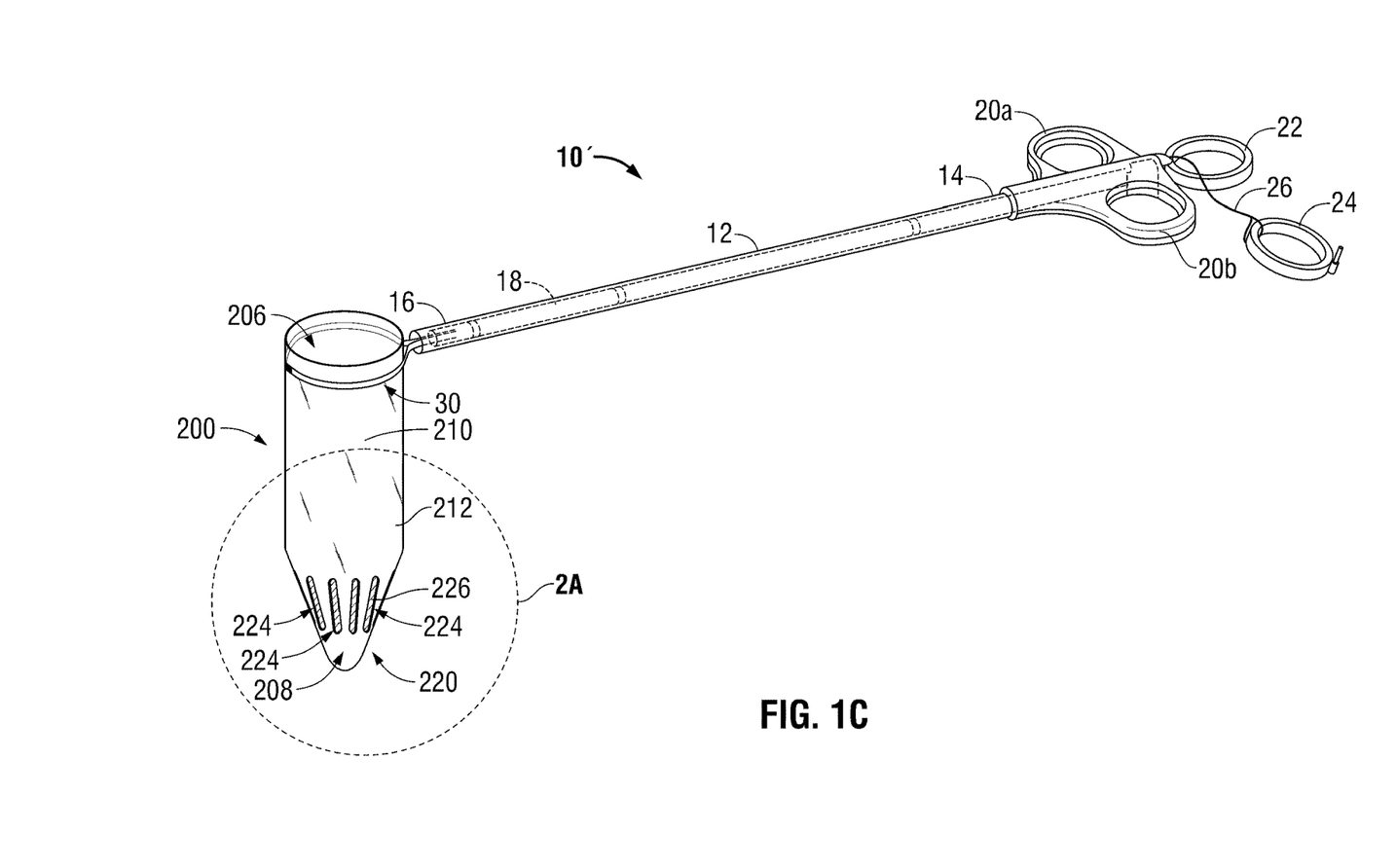
FIG. 1C is a perspective view of the specimen removal device of FIG. 1A including another embodiment of a pouch shown in a deployed configuration according to the present disclosure.

Referring now to the drawings, in which like reference numerals identify identical or substantially similar parts throughout the several views, FIGS. 1B and 1C illustrate a specimen removal devices 10 and 10' that are configured and dimensioned for use in minimally invasive surgical procedures (e.g. laparoscopic, endoscopic, and thoracic procedures). As shown in FIG. 1B, specimen removal device 10 includes an embodiment of a removal pouch 100, while FIG. 1C illustrates specimen removal device 10' with another embodiment of a removal pouch 200. A specimen removal device suitable for use in conjunction with either removal pouch is disclosed in, commonly owned, U.S. Pat. No. 5,647,372 to Tovey et al. and in U.S. Pat. No. 5,465,731 to Bell et al. and the entire contents of each is hereby incorporated by reference in their entirety.

Referring now to FIG. 1A, specimen removal device 10 is shown in an undeployed configuration and includes an elongated tubular member 12, a handle assembly 20, a drive rod 18 and a support member 30. Tubular member 12 slidably houses drive rod 18 and support member 30, which includes resilient support portions 32 and 34. Elongated tubular member 12 includes a proximal portion 14 and a distal portion 16. Proximal end 14 of tubular member 12 engages handle assembly 20, which tubular member 12 extends therefrom. Elongated tubular member 12 is configured and dimensioned for insertion through a small incision or a cannula 300 (FIGS. 4-7) for endoscopic or laparoscopic procedures.

Figure 6:
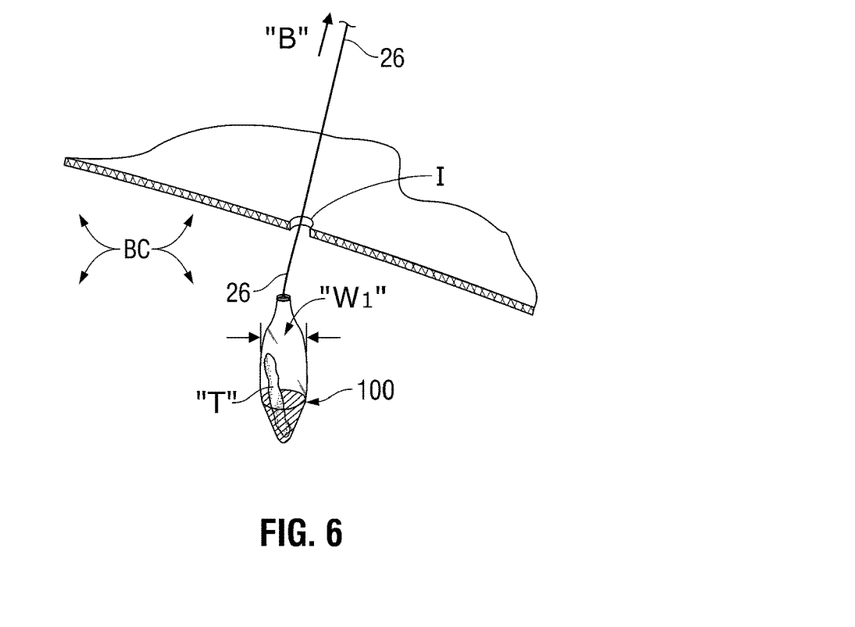
Figure 7:
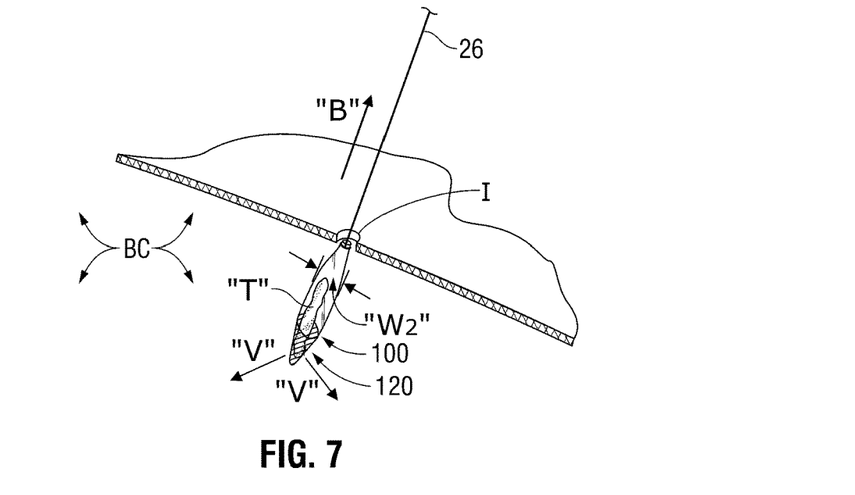

Handle assembly 20 includes handle portions 20a and 20b, a slidable finger loop 22 and a finger loop 24, which are each configured for ergonomically receiving fingers of a user. Handle assembly 20 also includes a drawstring 26 that is partially disposed within tubular member 12. Finger loop 24 is attached to one end of drawstring 26, as shown in FIGS. 1A-1C, while an opposing end of drawstring 26 is attached to a pouch 100 (FIGS. 6 and 7). Support member 30 forms a resilient spring loop configuration when resilient support portions 32 and 34 are connected. In the initial, unused or undeployed condition, pouch 100 is rolled up and the support member 30, including support portions 32 and 34, is in a relatively straight configuration and positioned within a distal portion 16 of tubular member 12 (FIG. 1A). In the deployed condition, pouch 100 is unfolded and connected support portions 32 and 34 expand to a loop configuration that supports pouch 100 (FIG. 1B), which will be further described in detail below.

Still referring to FIG. 1A, a locking tab 28 may be provided to prevent premature actuation of the surgical removal apparatus 10 (e.g., during shipping). Locking tab 28 is configured to engage a slot defined on drive rod 18 in a snap-fit manner (not shown). In this configuration, drive rod 18 is prevented from being pushed distally when locking tab 28 is engaged to drive rod 18 at a proximal end of handle portions 20a and 20b of handle assembly 20. To actuate surgical removal apparatus 10, the user (e.g., a surgeon) disengages locking tab 28, by pulling locking tab 28 off drive rod 18, and, subsequently, advances drive rod 18 in a distal direction, by pushing slidable finger loop 22 in a distal direction. When drive rod 18 is advanced distally, support member 30 is also advanced to a location distal than distal end 16 of tubular member 12, and resiliently opens to the loop formation, which thereby deploys and opens pouch 100, 200 attached thereto (FIGS. 1B and 1C).

Referring now to FIG. 1B, specimen removal device 10 is shown in a deployed configuration. In this configuration, support member 30 is in a distally, extended and deployed loop configuration, which thereby opens pouch 100 to an open configuration. Pouch 100 may be configured to have any suitable dimension for the purpose of collecting or entrapping specimen(s), for example, organ(s), tissue, and/or foreign objects from within a body cavity of a patient. Pouch 100 includes an elongated portion 110, an open proximal portion or mouth 106 and a closed distal portion 108. Elongated portion 110 is a flexible film or sheet formed from an elastomeric membrane, for example, but not limited to thermoplastic polyurethane (TPU). Elongated portion 110 may also be formed from a substantially transparent polymeric material, for example, but not limited to a polyurethane material. Additionally or alternatively, other biocompatible materials capable of forming a flexible membrane, such as latex, may be used. In embodiments, pouch 100 may be formed from an aromatic polyester type thermoplastic polyurethane. In addition, the material may be impervious to penetration by cancer cells.

Figure 2A:
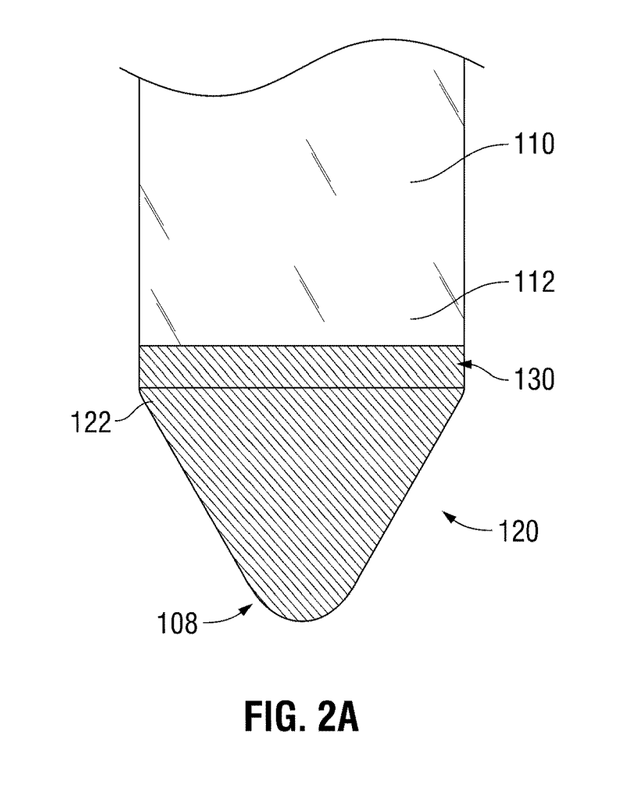
FIG. 2A is an enlarged view of the pouch of FIG. 1B according to the present disclosure.

Referring to FIGS. 1B and 2A, in accordance with an embodiment of the present disclosure, distal portion 108 of pouch 100 includes a gas vent 120 that is formed from a filter material. More specifically, a proximal end 122 of gas vent 120 is coupled to a distal end 112 of elongated portion 110 at a bonding region 130. It should be noted that the positioning of gas vent 120 is not limited to only the distal portion 108 of pouch 100 and gas vent 120 may be positioned at any portion of pouch 100. Gas vent 120 is made of a hydrophobic air filtering material or membrane. Additionally, gas vent 120 may be a porous and durable material (e.g., polyolefin fibers). In this configuration, gas (e.g., air) that is trapped within an interior portion of pouch 100 is released (e.g., venting) to an external environment (e.g., inside the body cavity) via gas vent 120, while retaining a tissue "T" (FIG. 5-7) within pouch 100. Further, when the trapped gas is effectively vented from within pouch 100 to the external environment, the volume of pouch 100 decreases to facilitate removal through a small laparoscopic incision or cannula 300 (FIGS. 4 and 6-8).

Additionally, a lubricious coating may be applied on the interior portion and/or the exterior portion of pouch 100. In this manner, the lubricious coating will facilitate removal of pouch 100 by decreasing friction between the exterior portion of pouch 100 and a small laparoscopic incision or cannula 300. Further, the lubricous coating will facilitate insertion of tissue "T" within the interior portion of pouch 100. The lubricous coating may be, for example, but not limited to, a hydrogel coating.

Referring now to FIG. 1C, specimen removal device 10' is shown in a deployed state. In this configuration, support member 30 is in the distally, extended and deployed loop configuration, which thereby opens pouch 200 to an open configuration. Pouch 200 may be configured to have any suitable dimension for the purpose of collecting or entrapping specimen(s), for example, organ(s), tissue, and/or foreign objects from within a body cavity of a patient. Similar to pouch 100, pouch 200 includes an elongated portion 210, an open proximal portion or mouth 206 and a closed distal end portion 208. Elongated portion 210 is a flexible film or sheet formed from an elastomeric membrane, for example, but not limited to thermoplastic polyurethane (TPU). Elongated portion 210 may also be formed from a substantially transparent polymeric material, for example, but not limited to a polyurethane material. Additionally or alternatively, other biocompatible materials may be used to form the flexible membrane of pouch 200, for example, but not limited to latex and polyisoprene. In embodiments, pouch 200 may also be formed from an aromatic, polyester-type thermoplastic polyurethane. In addition, the pouch material may be impervious to penetration by cancer cells.

Figure 2B:
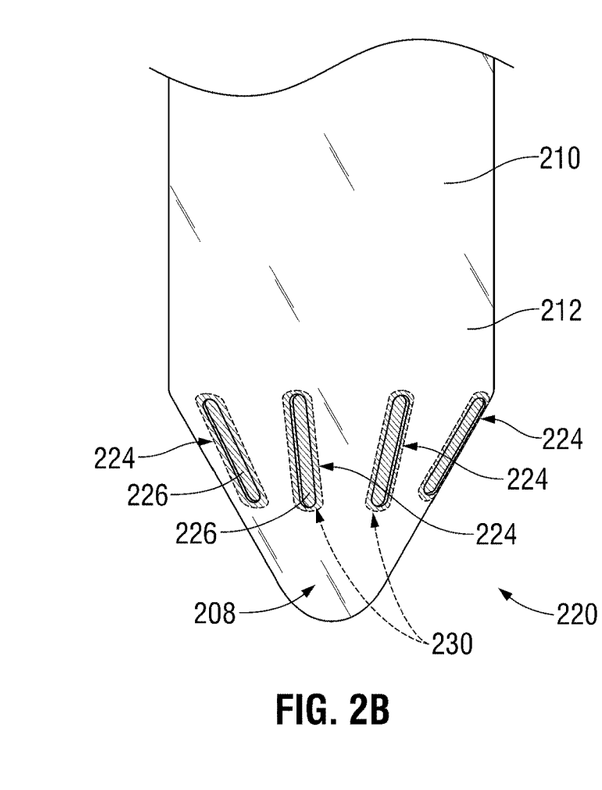
FIG. 2B is an enlarged view of the pouch of FIG. 1C according to the present disclosure.

Referring to FIGS. 1C and 2B, in accordance with another embodiment of the present disclosure, elongated portion 210 is dimensioned to have a distal portion 220 towards the distal portion 208. It should be noted that distal portion 220 may have any suitable shape (e.g., conical, round and square). Distal portion 220 includes one or more openings 224, which are each at least partially covered by a filter element 226. More specifically, filter element 226 overlaps opening 224 to adhere thereto at a bonding region 230. Similar to filter material used with gas vent 120 (FIG. 1B), each of filter elements 226 is made from a hydrophobic air filtering material or membrane. Additionally, each of filter elements 226 may be a porous and durable material (e.g., polyolefin fibers). In this configuration, air that is trapped within an interior portion of pouch 200 is released (e.g., venting) to an external environment (e.g., inside the body cavity) via one or more filter elements 226, while retaining a tissue "T" (FIG. 5-7) within pouch 200. Further, when the trapped gas is effectively vented from within pouch 200 to the external environment, the volume of pouch 200 decreases to facilitate removal through a small laparoscopic incision or cannula 300 (FIGS. 4 and 6-8).

For purposes of brevity, the attachment of the material used in conjunction with gas vent 120 and filter elements 226 to pouches 100 (FIG. 1B) and 200 will be described together. As such, various embodiments will be described, with regard to the attachment of the material used in conjunction with gas vent 120 and filter elements 226 to elongated portion 110, 220. In a first attaching technique, when elongated portion 110, 210 is made of a thermoplastic polyurethane (TPU), the material used in conjunction with gas vent 120 and filter elements 226 may be chemically attached to elongated portion 110, 210, respectively. More specifically, the TPU material of elongated portion 110, 210 is liquefied by dissolving the TPU material in a solvent (e.g., methylene chloride and tetrahydrofuran) such that the TPU material will act as a bonding compound. In this manner, the TPU material of elongated portion 110, 120 liquefies and penetrates pores of the material used in conjunction with gas vent 120 and filter elements 226. Once the solvent has evaporated, the TPU material of elongated portion 110, 210 securely attaches to the material used in conjunction with gas vent 120 and filter elements 226 at bonding region 130, 230, respectively.

In another attaching technique, the material used in conjunction with gas vent 120 and filter elements 226 may be attached to elongated portion 110, 210 at bonding region 130, 230 with the use of double-sided adhesive tape or biocompatible acrylic adhesive. In another attaching technique, the material used in conjunction with gas vent 120 and filter elements 226 may be attached to elongated portion 110, 210 with the use of RF welding of the material used in conjunction with gas vent 120 and filter elements 226 to elongated portion 110, 210 at bonding region 130, 230, respectively.

Figure 3:
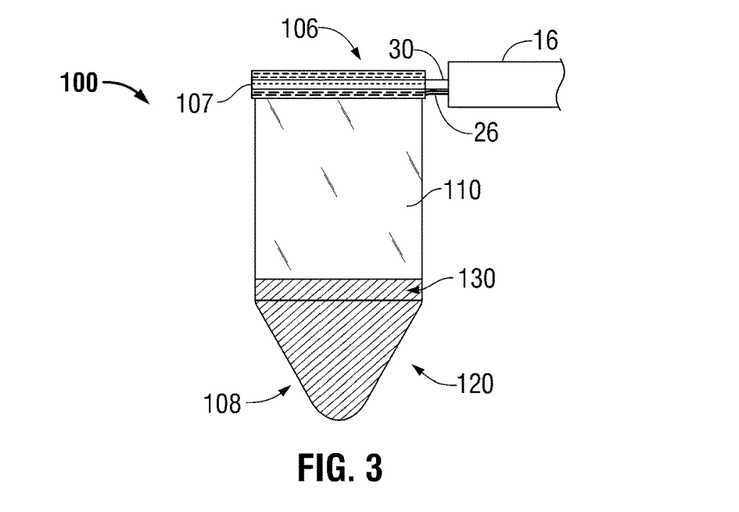
FIG. 3 is a side view of the pouch of FIG. 1B according to the present disclosure.

Referring now to FIG. 3, in accordance to other embodiments of the present disclosure, pouch 100 includes a linear portion 107 weakened by perforation or scoring, which extends circumferentially around mouth 106 of pouch 100 so that pouch 100 may be detachably released by pulling with sufficient force on finger loop 24 during a surgical operation when a user desires to detach pouch 100 from support member 30. In this manner, when finger loop 24 is pulled, drawstring 26 pulls off pouch 100 along the linear portion and detachably releases pouch 100 from support member 30 simultaneously with closure of mouth 106. Additionally or alternatively, structures also can be utilized to detach pouch 100 from support member 30, such as by pulling with a grasper or by cutting with a scissors.

Referring now to FIGS. 4-7, a method of using specimen retrieval devices 10 and 10' with the various embodiments of pouches 100 and 200 pouch will be described herein. For purposes of brevity, only specimen retrieval device 10 and pouch 100 will be described in the method indicated below. However, it should be noted that the aforementioned method may be used with any of the above-described specimen retrieval devices 10 and 10' along with any of the above-described pouches 100 and 200.

Figure 4:
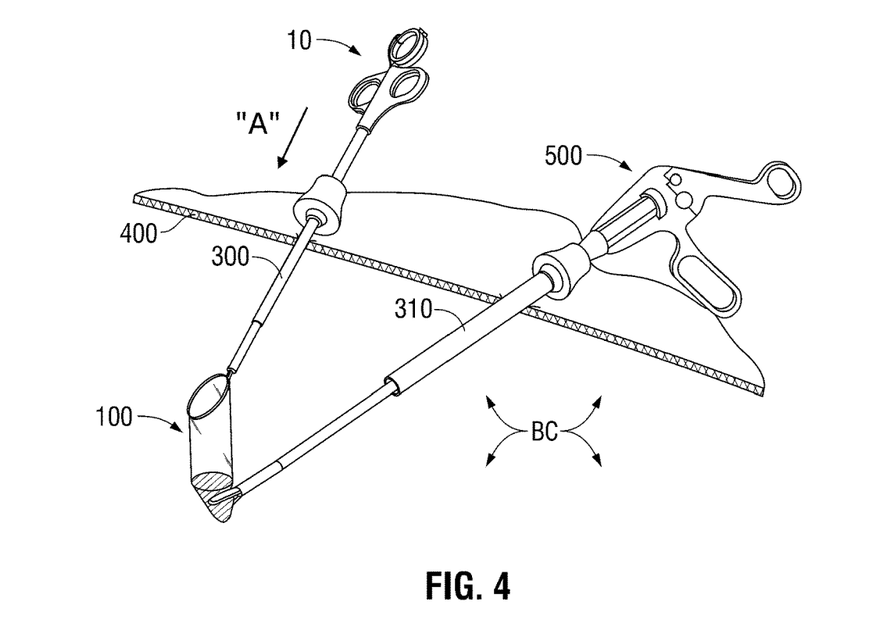
FIGS. 4-7 illustrate removal of the pouch of FIG. 1B from a body cavity according to an embodiment of the present disclosure.

FIG. 4 illustrates specimen retrieval device 10 being inserted within a cannula 300 in a distal "A" direction. Specimen retrieval device 10 is shown in a deployed state such that pouch 100 is in an open configuration to allow insertion of tissue "T" therewithin. FIG. 4 also illustrates a cannula 310 inserted within a skin layer 400 having a grasping instrument 500 that may be used to facilitate unfolding of pouch 100, placing specimen tissue "T" within pouch 100, or positioning pouch 100.

Figure 5:
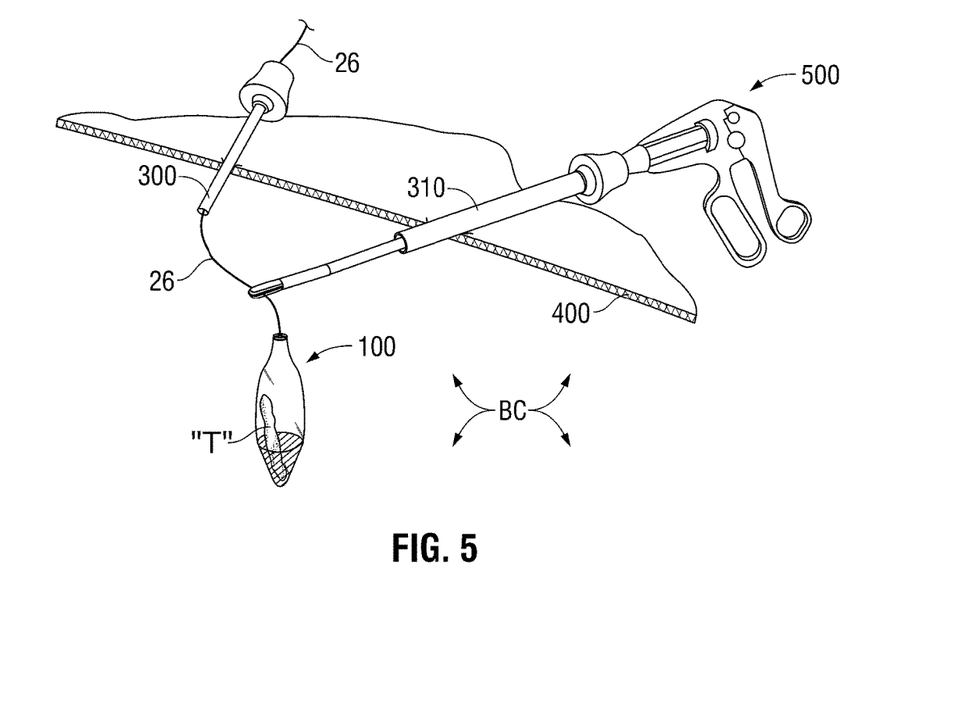

FIG. 5 illustrates pouch 100 having a specimen tissue "T" inserted therewithin. Pouch 100 is shown in a closed configuration to allow removal of pouch 100 from within a patient's body cavity "BC." As described above, pouch 100 is closed by pulling on drawstring 26 in a proximal direction. Grasping instrument 500 may be used to facilitate manipulation of pouch 100. One or more grasping instruments 500 may be utilized to grasp drawstring 26, pouch 100 and/or tissue "T" to facilitate insertion of tissue "T" within pouch 100 and/or removal of pouch 100 from within the body cavity "BC."

FIG. 6 illustrates pouch 100 being pulled towards an incision "I" by pulling drawstring 26 in a proximal direction, indicated by arrow "B." Prior to entering incision "I," pouch 100 is shown having air trapped therewithin the interior portion of pouch 100 and having a large width "W1." FIG. 7 illustrates pouch 100 being pulled into incision "I," which forces the dimension of pouch 100 to change to a smaller width "W2" than the previous width "W1." That is, when pouch 100 is pulled in a proximal "B" direction through a small opening (e.g., an incision "I"), the gas is vented out of pouch 100 through gas vent 120 in an outward "V" direction. In this configuration, the volume (e.g., width "W1") of pouch 100 is reduced when pulled through the incision "I" and/or an opening of cannula 300 (FIG. 5), thus, eliminating unnecessary gas pressure. In this manner, the chance of tearing or bursting filled pouch 100 is reduced and specimen tissue "T" prevented from spilling within the interior cavity of a patient during retrieval of pouch 100. Referring additionally to FIGS. 2A, 2B, it should be noted that gas vent 120 and the material used in conjunction with gas vent 120 and filter elements 226 of pouch 200 is configured to allow unidirectional flow of gases. For example, gases may only flow out of pouches 100 and 200 and not into pouch 100 and 200.

The surgical procedure being performed, the physical characteristics of the tissue sample "T" (e.g., size, mass, and density), and the volume of any liquids present in the pouch 100, 200 may be factors in determining the amount of gas that escapes through gas vent 120 and/or filter elements 226.

Although the above discusses one embodiment of the disclosed pouch, the techniques discussed are equally applicable to other embodiments of the pouch previously disclosed herein.

While the above description contains many specifics, these specifics should not be construed as limitations on the scope of the present disclosure, but merely as exemplifications of preferred embodiments thereof. For example, any of the disclosed filter elements described in the present disclosure may be positioned at any portion of the disclosed pouches. Those skilled in the art will envision many other possible variations that are within the scope and spirit of the present disclosure.

What is claimed is:

1. A method of removing a specimen from a fluid-filled location within a patient, the method comprising:
    inserting a specimen removal pouch through an incision of a patient to the fluid-filled location;
    moving a proximal mouth of the specimen removal pouch around the specimen such that the specimen and any fluid within the specimen removal pouch is at least partially positioned within a first portion of the specimen removal pouch;
    moving the proximal mouth from an open configuration toward a closed configuration to hinder the specimen from moving through the proximal mouth;
    removing the specimen removal pouch through the incision;
    releasing at least some of the fluid through a second portion of the specimen removal pouch, the second portion having a different porosity than the first portion; and
    filtering the fluid through the second portion of the specimen removal pouch.

2. The method according to claim 1, further comprising inserting the specimen removal pouch within a cannula.

3. The method according to claim 1, further comprising contacting the specimen removal pouch with a grasping instrument after the specimen removal pouch has been inserted through the incision.

4. The method according to claim 1, further comprising using a grasping instrument to position the specimen through the proximal mouth of the specimen removal pouch.

5. The method according to claim 1, wherein moving the proximal mouth from an open configuration toward a closed configuration is performed by pulling a drawstring.

6. The method according to claim 1, further comprising decreasing a width of the specimen removal pouch as the specimen removal pouch is removed through the incision.

7. The method according to claim 1, wherein the second portion of the specimen removal pouch includes a hydrophobic material.

8. The method according to claim 1, wherein the second portion of the specimen removal pouch is located at a distal portion of the specimen removal pouch.

9. The method according to claim 1, wherein the fluid that is released through the second portion of the specimen removal pouch is a gas.

* * * * *